(12) United States Patent
Rohde

(10) Patent No.: US 8,083,677 B2
(45) Date of Patent: Dec. 27, 2011

(54) ACCESS DISCONNECT DETECTION USING GLUCOSE

(75) Inventor: Justin B. Rohde, Des Plaines, IL (US)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 0 days.

(21) Appl. No.: 11/860,071

(22) Filed: Sep. 24, 2007

(65) Prior Publication Data
US 2009/0082653 A1    Mar. 26, 2009

(51) Int. Cl.
*A61B 5/00* (2006.01)
*A61B 5/05* (2006.01)
*A61M 37/00* (2006.01)

(52) U.S. Cl. .......... 600/371; 600/345; 604/4.01

(58) Field of Classification Search .......... 600/345, 600/347, 365, 371; 604/4.01
See application file for complete search history.

(56) References Cited

U.S. PATENT DOCUMENTS

| 4,140,963 | A | * | 2/1979 | Rao et al. .......... 324/442 |
| 4,545,382 | A | | 10/1985 | Higgins et al. |
| 5,262,035 | A | | 11/1993 | Gregg et al. |
| 5,522,977 | A | | 6/1996 | Shieh |
| 5,630,986 | A | | 5/1997 | Charlton et al. |
| 5,660,791 | A | | 8/1997 | Brenneman et al. |
| 5,665,222 | A | | 9/1997 | Heller et al. |
| 5,916,156 | A | | 6/1999 | Hildenbrand et al. |
| 6,294,281 | B1 | * | 9/2001 | Heller .......... 429/43 |
| 6,531,239 | B2 | | 3/2003 | Heller |
| 2005/0038325 | A1 | * | 2/2005 | Moll .......... 600/300 |
| 2006/0004271 | A1 | * | 1/2006 | Peyser et al. .......... 600/362 |
| 2006/0147763 | A1 | * | 7/2006 | Angenent et al. .......... 429/2 |
| 2007/0131546 | A1 | * | 6/2007 | Nomoto et al. .......... 204/403.01 |
| 2008/0065006 | A1 | | 3/2008 | Roger |
| 2008/0195021 | A1 | | 8/2008 | Roger |
| 2008/0195060 | A1 | | 8/2008 | Roger |
| 2008/0319287 | A1 | * | 12/2008 | Gross et al. .......... 600/316 |
| 2009/0079578 | A1 | | 3/2009 | Dvorsky |

(Continued)

FOREIGN PATENT DOCUMENTS
FR    2737124    1/1997

(Continued)

OTHER PUBLICATIONS

International Search Report for PCT/US2008/066092 filed Jun. 6, 2008 mailed Feb. 17, 2009.

(Continued)

*Primary Examiner* — Patricia Mallari
*Assistant Examiner* — Christian Jang
(74) *Attorney, Agent, or Firm* — K&L Gates LLP

(57) ABSTRACT

An access disconnect sensor for a patient undergoing extracorporeal blood processing includes an electrochemical fuel cell or sensor to detect blood leakage. The fuel cell includes circuitry for oxidizing glucose in the blood. The sensor also includes a transmitter to send a signal to a remote receiver that the sensor indicates the presence of blood. The circuitry may include a battery or may use electricity generated by the sensor to send a signal indicating a leak of blood or disconnection of the access needle.

15 Claims, 9 Drawing Sheets

U.S. PATENT DOCUMENTS

| | | |
|---|---|---|
| 2009/0080757 A1 | 3/2009 | Roger |
| 2009/0082646 A1 | 3/2009 | Bouton |
| 2009/0082647 A1 | 3/2009 | Busby |
| 2009/0082649 A1 | 3/2009 | Muller |
| 2009/0082676 A1 | 3/2009 | Bennison |
| 2009/0088612 A1 | 4/2009 | Bouton |
| 2009/0088613 A1 | 4/2009 | Marttila |
| 2009/0088683 A1 | 4/2009 | Roger |
| 2009/0105627 A1 | 4/2009 | Rohde |
| 2010/0022934 A1 | 1/2010 | Hogard |
| 2010/0022935 A1 | 1/2010 | Muller |

FOREIGN PATENT DOCUMENTS

| | | |
|---|---|---|
| WO | 03/063680 | 8/2003 |

OTHER PUBLICATIONS

Written Opinion of the International Searching Authority for PCT/US2008/066092 mailed on Feb. 17, 2009.

* cited by examiner

ACCESS DISCONNECT DETECTION USING GLUCOSE

BACKGROUND

The invention is in the field of medical treatments generally and patient vascular access systems. The present invention relates to embodiments of a method and a system for detecting blood leakage during extracorporeal blood treatment or other medical procedure.

The maxim of "first, do no harm," may be a good summary of the Hippocratic oath required of doctors and practiced by medical professionals. Nowhere is this principle required more than in modern medicine. With patients living longer, there are more extended treatments and more frail patients than ever. Such patients are in danger from complications that can arise from continuing therapeutic procedures, and even from diagnostic procedures, that are necessary for their continued care. Treatments involving extra-corporeal blood treatment are clear examples.

The most obvious danger is infection, but the harm caused by infection can be overcome by not re-using even supposedly-sterile devices and by diligent attention by the patient himself or herself, and by care givers attending to the patient. Other dangers also arise, but, like infections, have been difficult to eradicate. One of these dangers arises in blood treatment procedures in which the blood of a patient is physically removed from the patient for treatment, and then returned, all in the same procedure. Removal and return of blood is practiced in hemodialysis, for those persons whose kidneys do not function well. Other procedures, such as apheresis, involve removing blood from a patient or a donor to separate blood platelets or plasma from the red blood cells and then returning the red blood cells to the patient or donor, as described in U.S. Pat. Nos. 5,427,695 and 6,071,421.

The extracorporeal medical treatments described above require that the blood be removed for treatment and then returned. This requires access to the patient's vascular system, from which blood is removed and to which blood is then returned. If a "batch" treatment is used, that is, a quantity of blood is withdrawn, treated and returned, only a single needle is used. Each batch of such treatment is typically short, and the treatment is attended by a medical professional at a clinic or hospital. A variation on the batch treatment is a "batch" continuous method in which only a single needle is used. There are distinct withdraw and return phases in a batch continuous process. During the draw phase, blood is processed and additional blood is sent to a holding container to be processed during the return phase. In the return phase, blood is processed from the holding container and then returned to the patient or donor through the single needle. Other treatments are continuous, such as the platelet separation discussed above, or dialysis treatment, and may require a duration of several hours or even overnight.

Continuous treatments require two needles, or access points, one for withdrawal of blood and one for return. The withdrawal site is normally an artery or an arteriovenous fistula/graft, and a needle and a pump are used to provide the blood to the therapeutic machine. It is relatively simple to detect a problem with withdrawal, for instance, if the withdrawal needle is dislodged, using conventional air sensor technology. Detecting a problem in the return of the blood to the patient is more difficult. The return line typically includes a needle with venous access. If the return line is dislodged, the blood is not returned to the patient's vascular system, but may continue to be pumped and may accumulate near the patient. Depending on the pumping rate of the blood and the time for treatment, this could have life-threatening effects on the patient within a very short period of time.

Accordingly, a number of apparatuses have been devised for detecting needle dislodgement, especially venous needle dislodgement. An example is U.S. Pat. Appl. Publ. 2006/0130591. In a device according to this application, a venous needle is equipped with a photosensor and is covered with an opaque patch. This device would not send a signal or an alarm if the needle begins leaking or is only slightly dislodged. For example, the photosensor could still fail to detect light because the needle has not been dislodged sufficiently to expose the photosensor to light. In addition, this method requires ambient light and would thus not be suitable for patients that cover their arm with a blanket or who perform nocturnal dialysis while sleeping in a dark bedroom.

Numerous other techniques have been devised, many of them depending on a flow of blood causing conductivity between two electrodes or two wires. What is needed is a better way of quickly detecting dislodgement of a venous or other needle from a patient, so that inadvertent loss of blood and harm to the patient is avoided.

SUMMARY

One embodiment is a method of detecting blood leakage. The method includes steps of providing a glucose detector, mounting the detector adjacent an extracorporeal blood processing access site, taking a baseline reading from the detector on the access site on a patient, processing the baseline reading and determining a baseline, monitoring the detector for indications of blood leakage, and sending a signal if blood is detected.

Another embodiment is a method for detecting blood leakage at an access site. The method includes steps of providing a glucose detector, mounting the glucose detector near an access site on a patient, taking a baseline electrical reading of the access site with the glucose detector, processing the baseline reading and saving data of the baseline reading, monitoring the access site during a therapy procedure by taking additional electrical readings, and sending a signal if a reading indicative of a blood leak is detected.

Another embodiment is an access disconnect detector. The access disconnect detector includes a fuel cell having an anode and a cathode, a communications circuit connected to the fuel cell, optionally, a battery connected to at least one of the fuel cell and the communications circuit, and a mount suitable for mounting the fuel cell, the communications circuit, and the battery near an access site of a patient, wherein the fuel cell is configured for receiving blood leaking from the access site, causing oxidation of glucose in the blood, and causing the communications circuit to send a signal.

Another embodiment is an access disconnect detector. The access disconnect detector includes a glucose detector having an anode and a cathode, the anode comprising an anode electrolysis layer suitable for oxidation of glucose and the cathode comprising a cathode electrolysis layer. The detector also includes a communications circuit connected to the glucose detector, optionally, a battery connected to the glucose detector and the communications circuit, and a mount suitable for mounting the glucose detector, the communications circuit, and the battery near an access site of a patient, wherein the glucose detector is configured for receiving blood leaking from the access site, causing oxidation of glucose in the blood, thus generating electrical power and causing the communications circuit to send a signal.

Additional features and advantages are described herein, and will be apparent from, the following Detailed Description and the figures.

DETAILED DESCRIPTION

Figure 1:
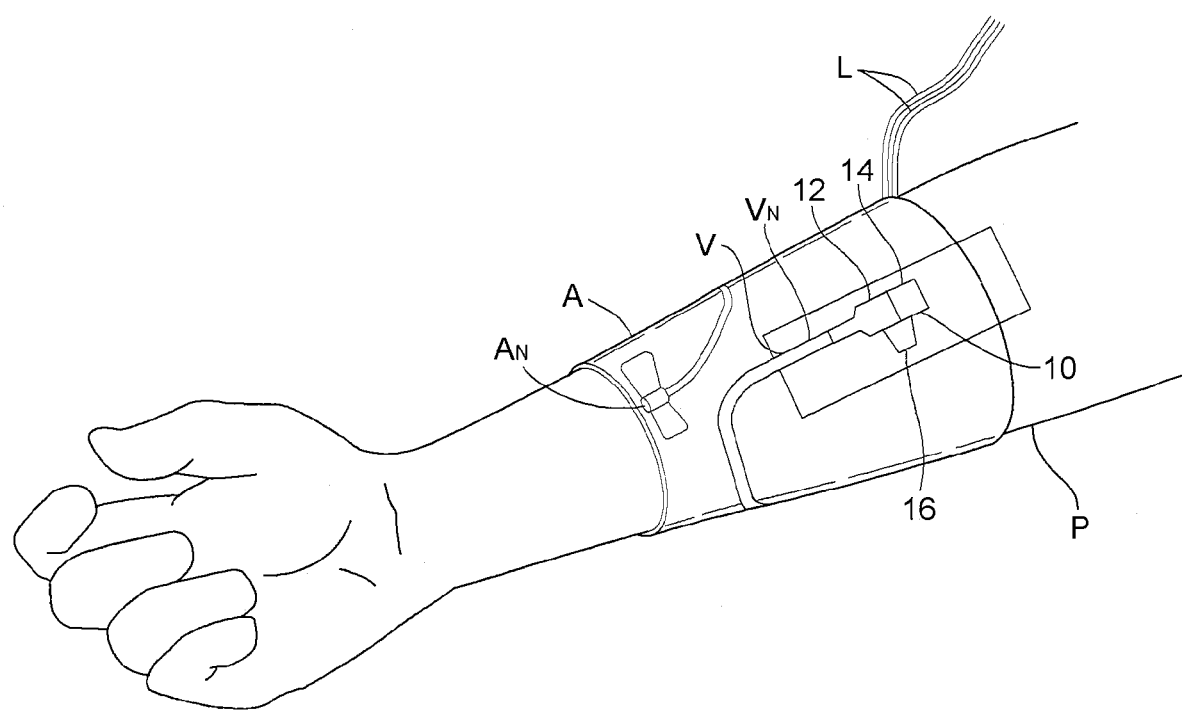
FIG. 1 depicts an embodiment of an access disconnect sensor.

Embodiments of the present invention are able to detect the presence of blood using the glucose in blood by means of an electrochemical detector. The presence of glucose alerts the patient or a caregiver of a blood leak at the access site. The electrochemical detector is a fuel cell, sometimes used for detecting and measuring a concentration of glucose in blood.

The details of the electrochemistry used in the detector are disclosed in the prior art, for example, U.S. Pat. No. 5,916,156, and U.S. Pat. No. 6,531,239. These patents disclose an electrochemical device that uses an oxidation/reduction reaction to oxidize glucose. In some embodiments, a simultaneous reaction also takes place with the reduction of oxygen in the blood to generate electricity. If instead the detector is powered with a battery, a periodic pulse or interrogation may be used to probe the detector. If blood is present, the pulse causes oxidation of the glucose with simultaneous reduction of a mediator present in the cell. In U.S. Pat. No. 5,916,156 (the '156 patent, which is hereby incorporated by reference as though each page and figure were set forth herein), the mediator provided is a ferrocyanine or $K_3Fe(CN)_6$. In a fuel cell intended for continuous generation of electricity, the cell may use the anode to oxidize glucose and the cathode to reduce oxygen, which is also present in the blood, and in the atmosphere surrounding the patient's access site. Such a cell is disclosed in U.S. Pat. No. 6,531,239 (the '239 patent, which is also incorporated by reference, as though each page and figure were set forth herein).

Glucose, a sugar, is a product of digestion of many foods and forms a natural part of the bloodstream, glucose normally being present in blood in a concentration from about 81 mg/dl to about 140 mg/dl. Persons with diabetes find it hard to control this concentration and must periodically correct their blood sugar by consuming sugar-containing drinks, such as orange juice, or by injecting insulin. Because of this medical problem, the technology for the detection and measurement of glucose in blood is highly advanced. The electrochemical cells discussed above are very small and lightweight, and may be used to detect blood, as well as to measure the concentration of species within the blood.

The '239 patent mentioned above contains a very detailed description of the chemical species required for continuous use as a fuel cell. The cell includes an anode and a cathode. Since this is in essence both a continuous and a biological fuel cell, the usual easy removal of reduced species (metal at the cathode) and oxidized species (gases at the anode) do not apply. Hence, the anode and cathode are provided with an electrolysis layer that allows for the mass transport of the species to and from the electrodes. Each electrolysis layer includes an enzyme and a redox polymer. Thus the anode electrolysis layer includes an anode enzyme and an anode redox polymer. The cathode electrolysis layer include a cathode enzyme and a cathode redox polymer.

Oxidation takes place at the anode, and the anode electrolysis layer facilitates the transport of glucose and the products of oxidation of glucose. Reduction takes place at the cathode, and the cathode electrolysis layer facilitates the transport of a species that are reduced, such as oxygen in hemoglobin and blood. Of course, in simpler embodiments, the cathode electrolysis layer may simply include a cathode and a reagent or species to be reduced at the cathode, and the anode electrolysis layer may simply include an anode species to be oxidized at the anode. An external electrical circuit transports electrons from the anode to the cathode.

In more complicated fuel cells, such as those described in the '239 patent, the electrolysis layer includes electrolysis redox polymers. The range of the redox potential for the anode redox polymer may be from about −0.65V to about +0.05V versus a standard calomel electrode. The anode redox polymer has a redox potential of at least 0.1 V positive of the redox potential of the anode enzyme. Useful anode redox polymers include $[(dmo)_2OsCl]^{+/2+}$, $[(ter)_2OsCl_2]^{0/+}$, and $[(trimetOsCl_2]^{0/+}$, coupled to either poly(1-vinyl imidazole) (PVI) or poly(acrylic acid), or a copolymer of 4-vinyl pyridine or 1-vinyl imidazole. In these formulae, dmo is 4,4'-dimethoxy-2,2'-bipyridine, ter is 2,2',2"-terpyridine, and trimet is 4,4',4"-trimethyl-2,2',2"-terpyridine.

The range of the redox potential for the cathode redox polymer is from about +0.3 V to about +0.7 V versus a standard calomel electrode. A known cathode redox polymer is $[(ter)(bpy)Os]^{2+/3+}$, coupled to poly(1-vinyl imidazole) or poly(4-vinyl pyridine). In this formula, bpy is 2,2'-bypyidine, and ter is 2,2',2"-terpyridine. Many other redox polymers are known. For example, a series of enzyme-type electrodes are disclosed in U.S. Pat. No. 5,262,035 (the '035 patent), which is hereby incorporated by reference as though each figure and page were physically set forth herein. These are primarily transition metal complexes, including derivatives of Os-(bpy)$_2$, pyridine complexes, and other metallocenes. One other known cathode redox polymer is Nafion® from DuPont. These may also be used in glucose monitors or glucose fuel cells used to detect the presence of blood.

Anode enzymes may include glucose oxidase, pyrroloquinoline quinone (PQQ) glucose dehydrogenase, galactose oxidase, pyrroloquinoline quinone fructose dehydrogenase, quinohemoprotein alcohol dehydrogenase, pyranose oxidase, oligosaccharide dehydrogenase, and lactate oxidase. Other enzymes may be used. Cathode enzymes may include peroxidase, tyrosinase, horseradish peroxidase, soybean peroxidase, laccases, and cytochrome C peroxidases.

For redox polymers, the preferred redox species is a transition metal compound or complex. The preferred transition metal compounds or complexes include osmium, ruthenium, iron, and cobalt compounds or complexes. In the preferred complexes, the transition metal is coordinatively bound to one or more ligands and covalently bound to at least one other ligand. The ligands are often mono-, di-, tri-, or tetradentate. The most preferred ligands are heterocyclic nitrogen compounds, such as, for example, pyridine and/or imidazole derivatives. For example, the multidentate ligands typically include multiple pyridine and/or imidazole rings. Alternatively, polymer-bound metallocene derivatives, such as, for example, ferrocene, can be used. An example of this type of redox polymer is poly(vinylferrocene) or a derivative of poly (vinylferrocene) functionalized to increase swelling of the redox polymer in water. Experimental work on the above materials, studying the oxidation of glucose, revealed voltages and current densities ranging up to 1100 μamps/cm$^2$ at about 0.4 volts. See '035 patent, cols. 9-11. This demonstrates useful and detectable amperages at reasonable voltages.

Figure 2:
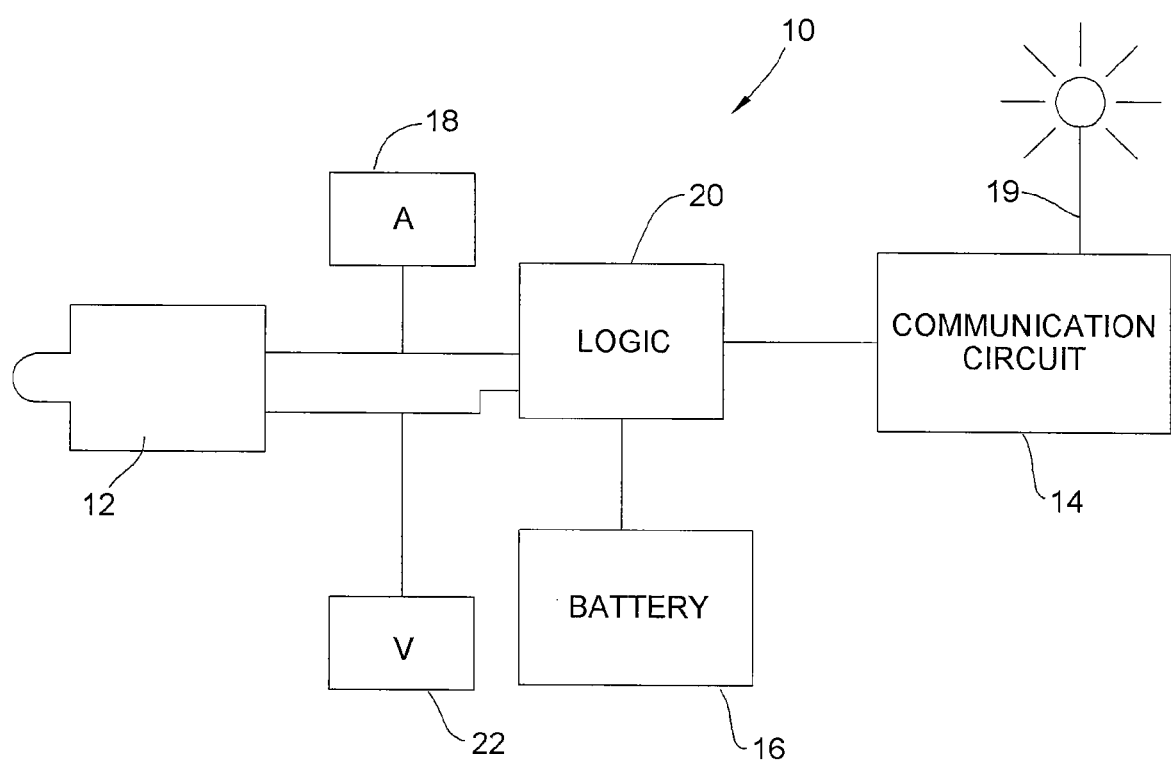
FIG. 2 depicts details of the sensor of FIG. 1.

An embodiment of an electrochemical sensor for use at an access site is depicted in FIG. 1. A patient P undergoing hemodialysis or other extracorporeal therapy is connected to the therapy machine (not shown) via blood lines L. The access site includes arterial access A with needle $A_n$ and venous access V with needle $V_n$. The access site has been equipped with an electrochemical blood detector 10, the detector including a sensor 12, a wireless communications circuit 14, and a battery 16. As seen in the closer look in FIG. 2, detector 10 includes the sensor 12 itself, an ammeter 18 and voltmeter 22, and a logic circuit 20, along with a battery and a communications circuit 14. The communication circuit is depicted as having an antenna 19, and is thus wireless. Other embodiments may use a tether or cable between the sensor and a power supply and communications module, or between the sensor and the therapy machine with a power supply and communications capabilities.

The wireless transmitter is small and compact, and is easily placed on the patient at the access site and connected to the electrochemical sensor. One module with good capabilities is a wireless module in accord with ZigBee/IEEE 805.15.4. This is a standard for a very low power radio system with a very limited range, about 10-20 feet. Modules made in accordance with this standard may be purchased from Maxstream, Inc., Lindon, Utah, U.S.A., Helicomm, Inc., Carlsbad, Calif., U.S.A., and ANT, Cochrane, Alberta, Canada. The module is very small, and may be about 2 cm square (about 1 inch square), and about 3 mm thick (⅛ inch). The transmitter may be used to communicate with the therapy machine or with a separate receiver or controller dedicated to monitoring the sensor.

The circuit used with the sensor may take on many forms. It may not be necessary to use a battery, since the sensor generates energy rather than uses energy. This embodiment would allow for a reduced size and cost of the device, as well as increased comfort for the patient using this device near his or her access site. However, with a power supply, it is easier to monitor the "health" of the sensor. For example, by taking periodic readings of the normally quiescent voltage and amperage of the sensor. Without a power supply, it may be difficult to know whether the sensor is broken rather than simply in a state in which blood has not been detected, and therefore glucose is not available to power the detector. Accordingly, the detector may be equipped with a battery as shown, but it is not strictly necessary for operation of the detector.

As noted above, the sensor is actually a fuel cell, creating electricity by reacting glucose and other materials and producing electrochemical reactions. Accordingly, it should be possible to sample the cell for the voltage difference across the anode and cathode, and also to sample the current produced by the cell. These voltage and current measurements are used by glucose meters to determine the concentration of glucose in a person's blood. In the present application of the glucose fuel cell, such accuracy is not needed, but can be used to determine the presence and the extent of the leak or blood that is present. Accordingly, the detector circuit can include an ammeter 18 and a voltmeter 22. It will be recognized that these circuits, including control circuit 20, will desirably be placed on a semiconductor chip, as part of an integrated circuit, to make them very small. In this manner, the sensor and the detector will both be very small and as unobtrusive as possible to the patient.

Figure 3A:
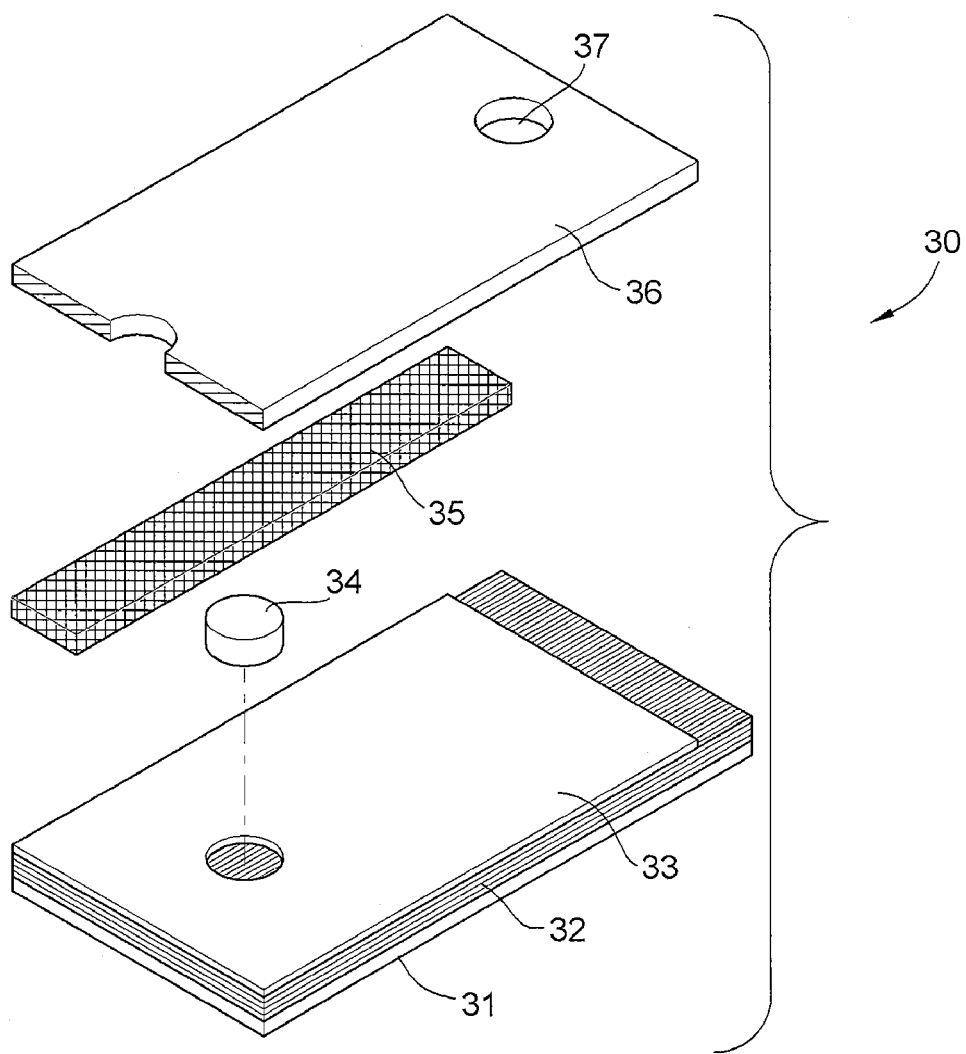
FIG. 3 is an exploded view of layers of a glucose fuel cell.
Figure 3B:
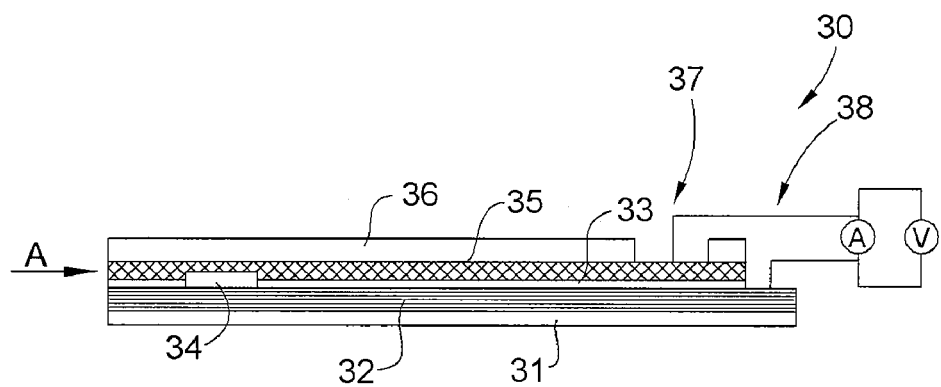

An example of a glucose powered sensor is depicted in FIGS. 3A and 3B. In FIG. 3A, sensor 30 includes top and bottom polycarbonate layers 31, 36, with aperture 37 in the top layer. Layer 32 is the anode. In one embodiment, layer 32 is made from a conductive graphite sheet. Layer 33 is a double-sided adhesive tape that joins anode 32 and cathode 35 while also insulating them from one another. The cathode is made from a permeable graphite web, including cross-linked polyvinyl alcohol and carbon fibers. Reagent pellet 34 is a polymeric (nylon) membrane that is impregnated, in separate steps, with both potassium hexacyanoferrate ($K_3Fe(CN)_6$) and with glucose oxidase. The glucose oxidase is a solution made from glucose oxidase, surfactant, citrate buffer and polyethylene oxide (MW 300,000). As seen in side view FIG. 3B, the aperture 37 provides a path for a connection to the cathode 35, while a gap 38 on one end of the sensor provides a path for a connection to the anode 32.

Sensors with this configuration may be made very small, having an area of a few square millimeters, with the aperture being about 3 millimeters diameter. Blood enters the sensor as shown by arrow A, and is wicked into the sensor through the graphite web 35. The blood contacts reagent pellet 34, the pellet including glucose oxidase and potassium hexacyanoferrate. The net reaction is that glucose, catalyzed by the glucose oxidase enzyme, reacts with the potassium hexacyanoferrate. At the anode, the glucose+glucose oxidase is oxidized, generating electrons, i.e., a current, while at the cathode, potassium hexacyanoferrate is reduced, thus completing the circuit. This current is measured by an external circuit, that can also monitor the voltage of the circuit. The chemical potential of the glucose is thus used to power the sensor and generate a measureable current.

Figure 4:
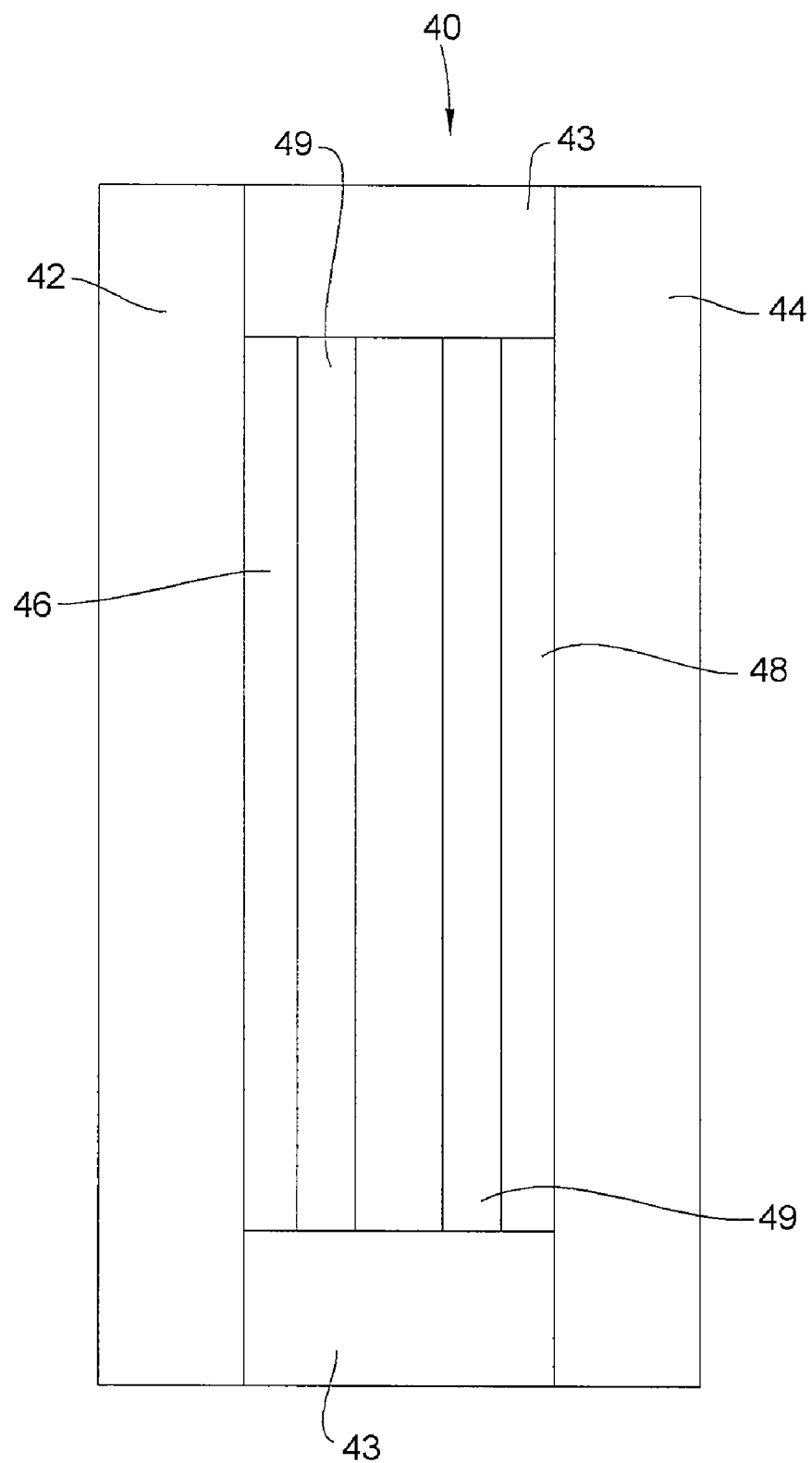
FIGS. 4-6 depicts additional embodiments of anodes and cathodes for a glucose fuel cell.
Figure 5:
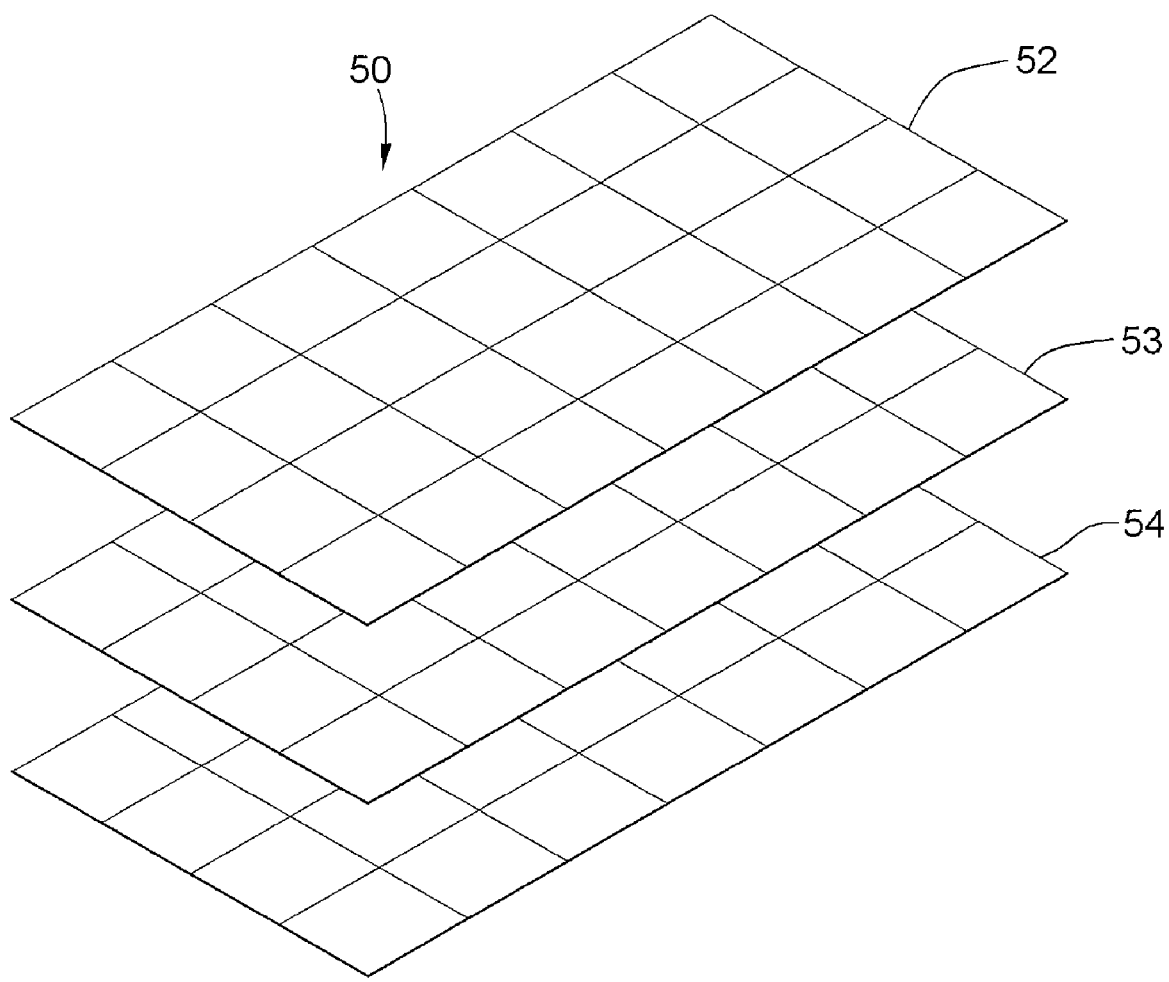
Figure 6:
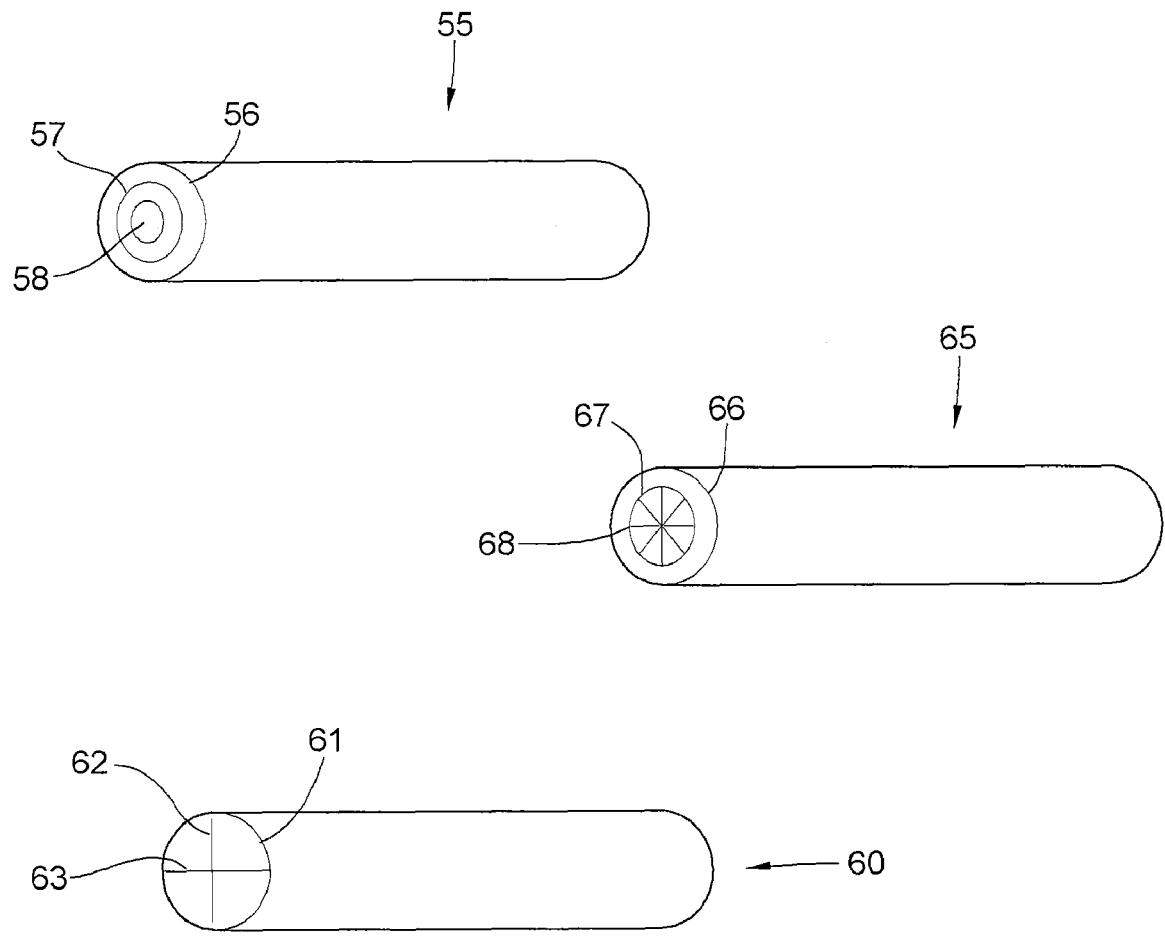

The more complicated examples given above, with enzymes and electrolysis layers, may also be used. Examples of fuel cells/sensors with these circuits are depicted in FIG. 4-6. In FIG. 4, sensor 40 includes an anode 42, a cathode 44 and separators 43. The separators may be made from inert, non-conductive materials, while the anode and cathode are as described above. An anode electrolysis layer 46 is adjacent anode 42 and a cathode electrolysis layer 48 is adjacent cathode 44. The electrolysis layers may have a coating 49 to keep out undesirable macromolecular materials and help to insure the long life of the sensor. In one embodiment, the coating may be a porous hydrogel made from cross-linked poly(ethylene oxide). FIG. 4 has a planar shape. The fluid of interest may flow through the center between the coatings, or the electrodes may be porous allowing the fluid to flow through or into the electrodes.

FIG. 5 depicts an embodiment in which the electrodes are made from mesh-type materials. Cell 50 includes an anode 52, a cathode 54, and a non-conductive separator 53. In FIG. 6, tubular or cylindrical sensors are disclosed. Sensor 55 includes an outer anode 56, a central cathode 58 and a spacer 57 between them. Sensor 65 includes an outer anode 56, an inner cathode 68 that includes a plurality of plates, and a tubular non-conductive spacer 67. This embodiment has additional surface area and would be expected to have the potential for greater current. Finally, sensor 60 includes an outer anode 61, a planar cathode 62, and an intersecting planar separator 63, the separator longer than cathode 62 to ensure separation from anode 61.

Figure 7:
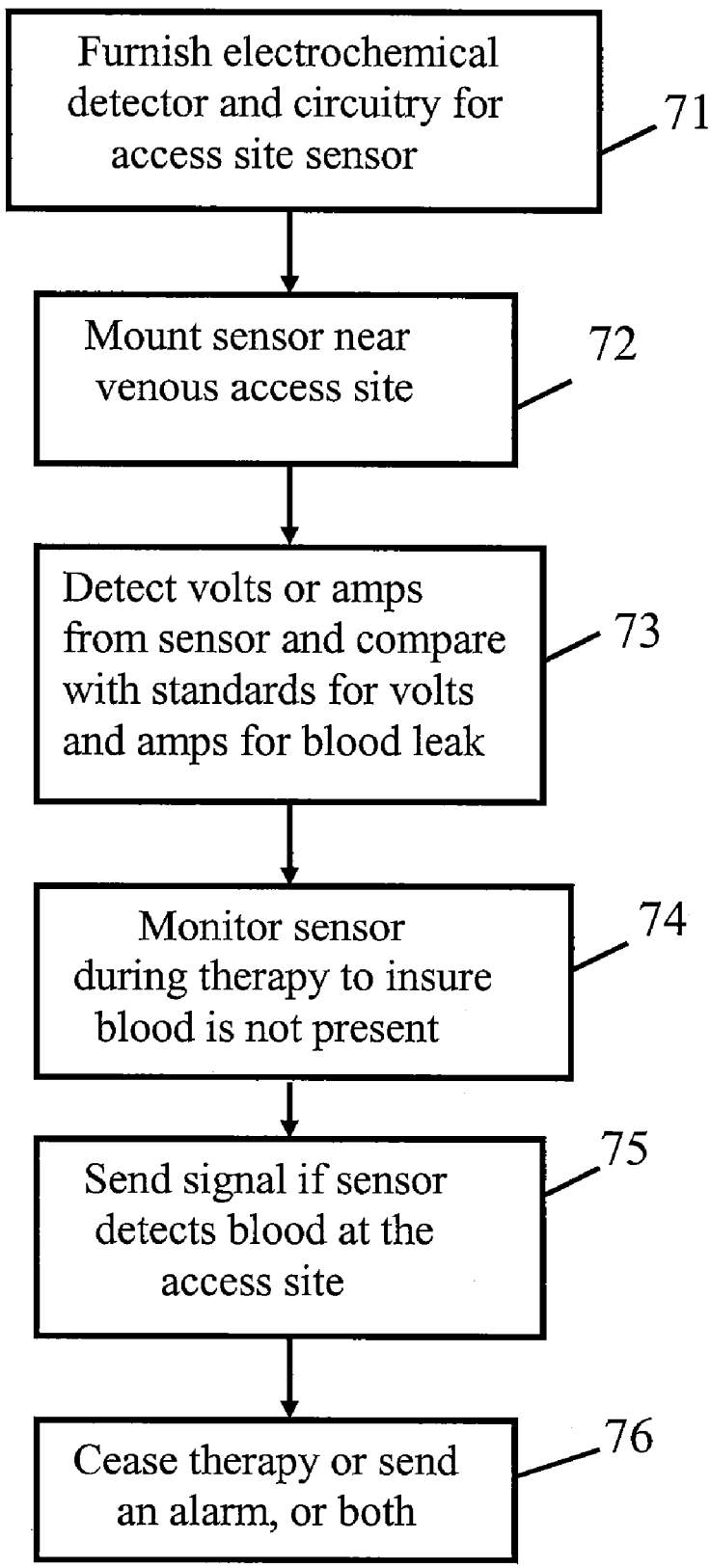
FIG. 7 depicts a flowchart for a method of using the disconnect sensor.

Embodiments include methods of using the electrochemical sensor. In one method, depicted in FIG. 7, a user furnishes 71 an electrochemical detector along with circuitry for the sensor. The user or a caregiver mounts 72 the sensor near or atop a venous access site. The sensor is activated and baseline or initialization readings may be taken. The detecting circuitry then detects 73 electrical signals, such as volts or amps, from the sensor. Software in a control circuit then compares these signals to the expected, standard or baseline signals to determine whether blood is present at the sensor. In embodiments with a battery, the baseline signal may be a reading of no current and no voltage. As therapy continues, the sensor is monitored 74 to insure that blood is not present at the access site, that is, blood that would be indicated by a reaction of the cell to glucose in blood. If the sensor encounters glucose from blood at the access site, an amperage or voltage is generated and a signal 75 is sent to control circuitry of the hemodialysis or other therapy machine, or a controller in communication with the therapy machine. The control circuitry then can cease therapy 76, i.e., stop pumping blood, alert a caregiver, sound an alarm, or take other action.

Figure 8:
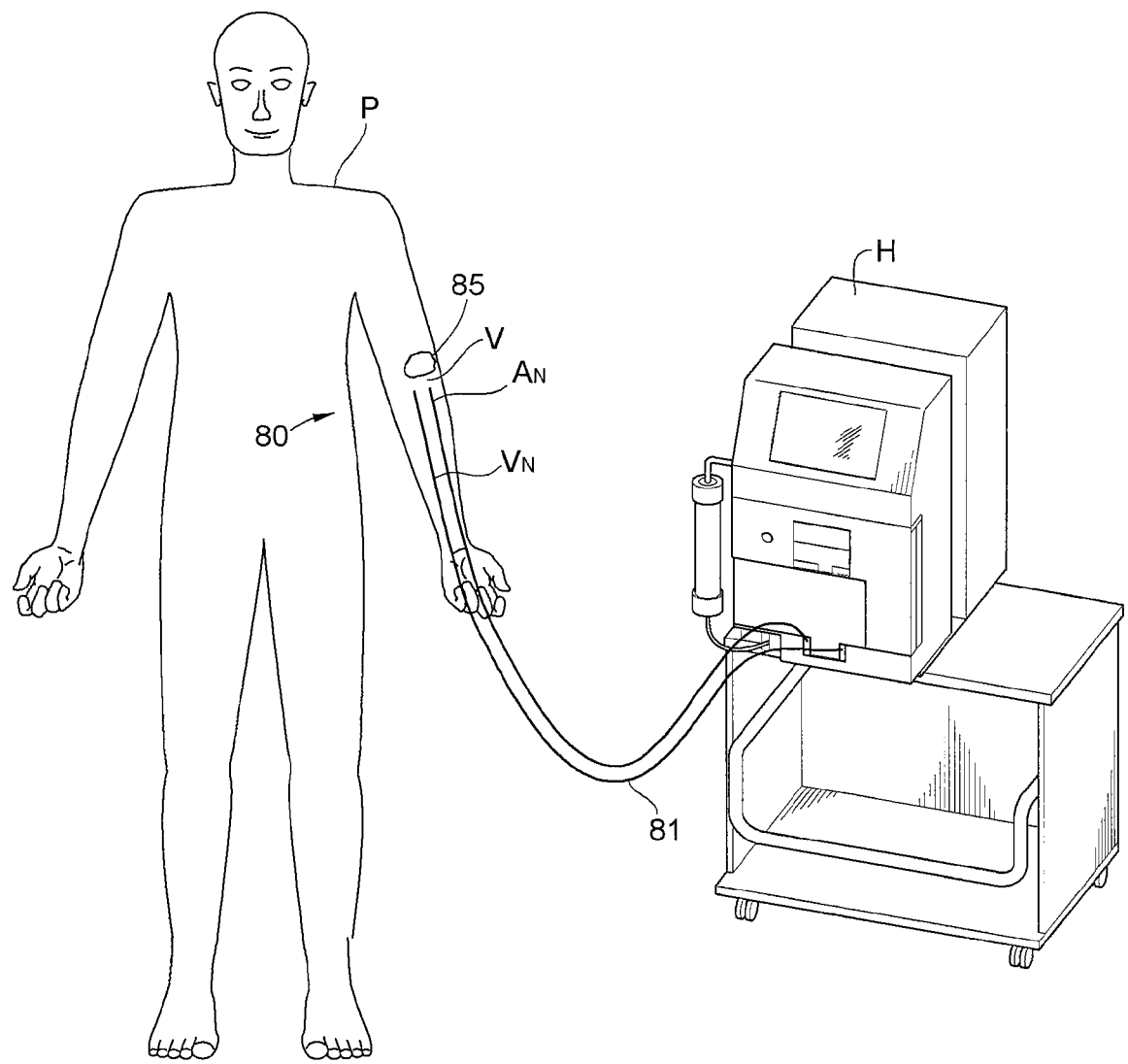
FIG. 8 depicts the electrochemical sensor used with a hemodialysis machine.

The sensors may be used, as mentioned, with a therapy machine, such as a hemodialysis machine. FIG. 8 depicts a combination 80 of a hemodialysis machine H operably connected with an electrochemical sensor 85. The hemodialysis machine is connected to the patient P with blood lines 81. The tubing of the blood lines are attached to the patient at the arterial access site A with arterial needle $A_n$ and at the venous access site V with venous needle $V_n$.

Figure 9:
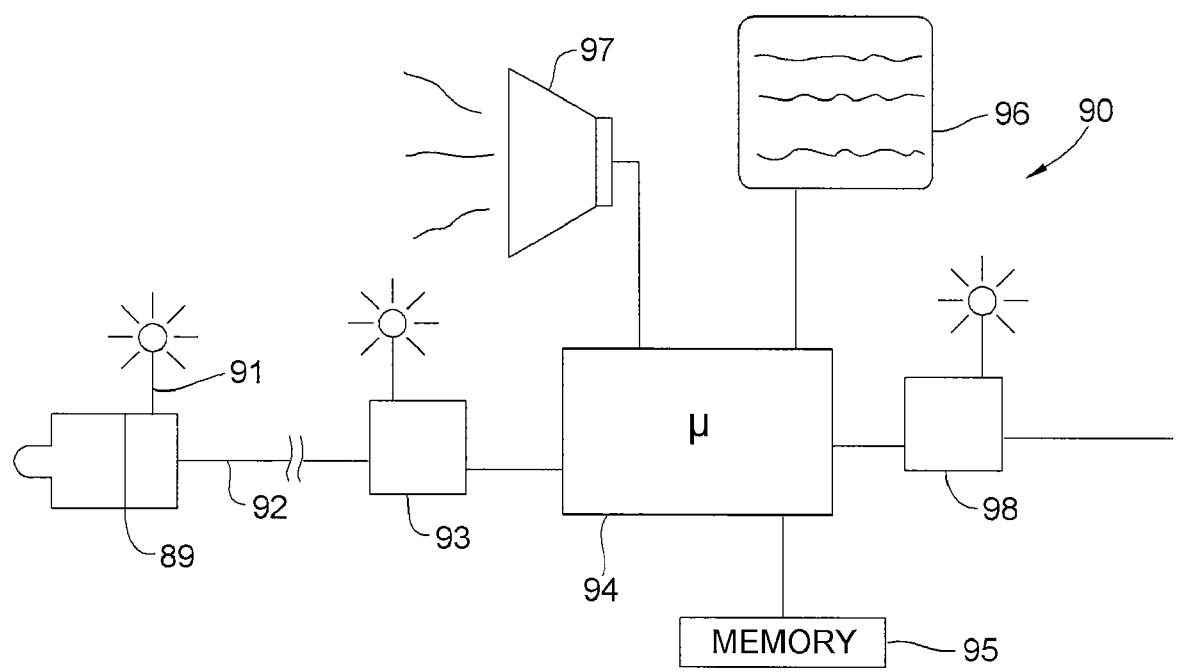
FIG. 9 is a schematic depiction of control circuitry for the sensor.

Control circuitry that receives a signal from the electrochemical sensor and its transmitter is depicted in FIG. 9. As noted above for FIG. 1, glucose sensor embodiment 89 may have a radio communication link, through antenna 91, or may be connected via a wire connection or cable 92. Control circuitry 90 for receiving a signal from the sensor 89 includes an interface 93 for receiving a signal, which may be an amplifier, a multiplexer, or other signal interface circuitry. Interface 93 may also include an antenna for receiving a wireless signal from the glucose sensor. The signal is then sent to microcontroller 94 for comparison with standards stored in a memory 95. Microcontroller 94 is also in communication with local outputs, such as a video screen 96 and a speaker 97, which may be used to alert the patient or a caregiver when blood is detected by the glucose sensor. Control circuitry 90 also includes an output communications circuit 98, which can output a signal wirelessly or through a wired link. The output communications circuit may be used to communicate with a hospital information system, a clinic information system, or other network.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

What is claimed is:

1. An access disconnect detector, comprising:
a fuel cell having an anode and a cathode, the fuel cell configured to generate electrical signals and receive only blood for power;
a control circuit connected to the fuel cell, the control circuit configured to receive the electrical signals generated by the fuel cell and compare the electrical signals to predetermined values, wherein the control circuit includes a memory storing the predetermined values;
a communications circuit connected to the fuel cell; and
a mount suitable for mounting the fuel cell and the communications circuit near an access site of a patient, wherein the fuel cell is configured for receiving blood leaking from the access site and producing electrical power upon receiving the leaking blood, thus causing the communications circuit to send a signal, indicating an access disconnection.

2. The access disconnect detector of claim 1, wherein the anode is configured for oxidizing at least one of glucose and glucose oxidase.

3. The access disconnect detector of claim 1, wherein the cathode is configured for reducing potassium hexacyanoferrate.

4. The access disconnect detector of claim 1, wherein the communications circuit is in operable communication with a hemodialysis machine, and further comprising the hemodialysis machine.

5. The access disconnect detector of claim 1, further comprising a local output device to alert a person or to sound an alarm.

6. The access disconnect detector of claim 1, wherein the cathode is permeable and is configured to wick blood into an inside of the fuel cell.

7. The access disconnect detector of claim 1, wherein the fuel cell is a glucose detector.

8. An access disconnect detector, comprising:
a glucose detector having an anode and a cathode, the anode comprising an anode electrolysis layer suitable for oxidation of glucose and the cathode comprising a cathode electrolysis layer, the glucose detector being powered exclusively by blood;
a control circuit connected to the glucose detector, the control circuit configured to receive electrical signals generated by the glucose detector and compare the electrical signals to predetermined values, wherein the control circuit includes a memory for storing the predetermined values;
a communications circuit connected to the glucose detector; and
a mount suitable for mounting the glucose detector and the communications circuit near an access site of a patient, wherein the glucose detector is configured for receiving blood leaking from the access site and generating electrical power upon receiving the leaking blood, the power causing the communications circuit to send a signal upon detecting the leaking blood, indicating an access disconnection.

9. The access disconnect detector of claim 8, wherein the anode electrolysis layer comprises an anode enzyme and an anode redox polymer.

10. The access disconnect detector of claim 9, wherein the anode enzyme is selected from the group consisting of glucose oxidase, pyrroloquinoline quinone glucose dehydrogenase, galactose oxidase, pyrroloquinoline quinone fructose dehydrogenase, quinohemoprotein alcohol dehydrogenase, pyranose oxidase, oligosaccharide dehydrogenase, and lactate oxidase.

11. The access disconnect detector of claim 8, wherein the cathode electrolysis layer comprises a cathode enzyme and a cathode redox polymer.

12. The access disconnect detector of claim 11, wherein the cathode enzyme is selected from the group consisting of a peroxidase, tyrosinase, horseradish peroxidase, soybean peroxidase, a laccase, and cytochrome C peroxidases.

13. The access disconnect detector of claim 8, wherein the mount is a flexible pad, and further comprising an absorbent layer adjacent the glucose detector.

14. The access disconnect detector of claim 8, further comprising a battery connected to the glucose detector and the communications circuit.

15. The access disconnect detector of claim 8, wherein the glucose detector causes oxidation of glucose in the blood detected.

* * * * *